United States Patent
Woodward et al.

(10) Patent No.: US 6,277,846 B1
(45) Date of Patent: Aug. 21, 2001

(54) USE OF PLATELET ACTIVATING FACTOR ANTAGONISTS AS ANTI-PRURITIC AGENTS

(75) Inventors: David F. Woodward, Lake Forest; Linda Sue Williams, Santa Ana, both of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/138,967

(22) Filed: Aug. 24, 1998

Related U.S. Application Data

(63) Continuation-in-part of application No. 07/837,568, filed on Feb. 18, 1992, now abandoned, which is a continuation of application No. 07/530,739, filed on Mar. 31, 1990, now abandoned.

(51) Int. Cl.$^7$ .................................................. A61K 31/55
(52) U.S. Cl. .................. 514/219; 514/234.5; 514/237.5; 514/357; 514/449; 514/461; 514/468; 514/470; 514/886; 514/887
(58) Field of Search ..................................... 514/449, 461, 514/468, 470, 886, 887, 357, 219, 234.5, 237.5

(56) References Cited

U.S. PATENT DOCUMENTS

| | | | |
|---|---|---|---|
| 4,734,280 | 3/1988 | Braquet | 424/195.1 |
| 4,820,703 | 4/1989 | Tahara et al. | 514/220 |
| 5,334,592 * | 8/1994 | Billah | 514/220 |

FOREIGN PATENT DOCUMENTS

| | | |
|---|---|---|
| 0157609 | 10/1985 | (EP) . |
| 8910143 * | 2/1989 | (WO) . |
| 9118608 * | 12/1991 | (WO) . |

OTHER PUBLICATIONS

Woodward et al., *Models in Dermatology 1*, 187–195 (1985).
Herndon, J.H., Jr., *Int. J. Derm.* 14, 465–484 (1975).
Winkelmann, R.K., *Med. Clins. N. Am.* 66, 1119–1133 (1982).
Cormia, F.E., *J. Invest. Derm.* 19, 21 (1952).
Shelley, W.B. and Arthur, R.P., *Arch. Derm.* (Chicago) 76, 296, 323 (1957).
Hagermark et al., *J. Invest. Dermatol.* 69, 527–539 (1977).
Hagermark, *Acta Dermatovener* 53, 363–368 (1973).
Fjellner and Hagermark, *Acta Derm. Venereol.* 65, 409–412 (1985).
Hanahan and Kumar, *Prog. Lipid Res.* 26, 1–28 (1987).
Terashita et al., *J. Pharm. Exp. Ther.* 242, 263–268 (1987).
Fjellner, Experimental and Clinical Pruritus, 1981.
Ferreira, Nature New Biology, vol. 240, Dec. 13, 1972.
Greaves et al., Brit. Med. J. 3 (5881): 608–9, Sep. 1973.
Roberts, et al., J. Allergy Clin. Immunol., August 1988, 236–241.
Keele, et al., Substances Producing Pain and Itch, Chapter 2, The Williams & Wilkins Co., 1964.
Boss, et al., Arch. Dermatol., vol. 117, Apr. 1981.
Pipkorn, et al., Allergy, 1984, 39, 141–5.
Archer, et al., British Journal of Dermatology, (1985), 112, 285–90.
Henocq, et al., The Lancet, Jun. 14, 1986, 1378–9.
Chung, et al., The Lancet, Jan. 31, 1987, 248–50.
Guinot, et al., Prostaglandins, Jul. 1986, vol. 32, No. 1, 160–163.
Shuhei Miyazawa et al, Chem. Pharm. Bull, 39 (12), 1991, pp. 3215–3220.
Woodward et al, J. Pharmacol. Exp. Ther., Characterization of a Behavioral Model for Peripherally Evoked Itch Suggests Platelet–Activating Factor as a Potent Pruritogen, 272, pp. 758–765, (1989).
Woodward et al, Eur, J. Pharmacol., Platelet–activating factor causes goblet cell depletion in the conjunctiva, 168 (23), 1989, pp. 23–30.

* cited by examiner

*Primary Examiner*—Dwayne C. Jones
*Assistant Examiner*—C. Delacroix-Muirheid
(74) *Attorney, Agent, or Firm*—Cynthia H. O'Donohue; Robert J. Baran; Martin A. Voet

(57) ABSTRACT

The invention relates to a method for treating pruritus by administering a therapeutically effective amount of a PAF antagonist to a mammal afflicted with pruritus. The PAF antagonists may, for example, be selected from synthetic PAF analogues, natural products isolated from plants having PAF antagonist activity, and triazolobenzodiazepines. The PAF antagonists are preferably applied topically to the afflicted site but systemic such as oral, parenteral, nasal and intrarectal administration, is also possible.

25 Claims, No Drawings

USE OF PLATELET ACTIVATING FACTOR ANTAGONISTS AS ANTI-PRURITIC AGENTS

RELATION BACK

This is a continuation-in-part of application Ser. No 07/837,568, filed on Feb. 18, 1992, now abandoned, which is in turn a continuation of application Ser. No. 07/530,739, filed on Mar. 31, 1990, now abandoned.

FIELD OF THE INVENTION

The present invention relates to methods and means for treating pruritus. More particularly, this invention concerns the use of platelet activating factor (PAF) antagonists or anti-pruritic agents.

BACKGROUND OF THE INVENTION

Itch, or pruritus, is a common and distressing symptom in a variety of diseases. Pruritus typically occurs in peripheral diseases such as allergic conjunctivitis, allergic rhinitis, hemorrhoids, and dermatoses of fungal, allergic and non-allergic origin. Itching can also be a major symptom of certain systemic diseases such as, Hodgkin's disease, chronic renal failure, polycythema vera, hyperthyroidism and cholestasis (see, for example, Herndon, J. H. Jr., Int. J. Derm. 14, 465–484 (1975); Winkelmann, R. K., Med. Clins. N. Am. 66, 1119–1133 (1982)]. The clinical importance of pruritus is undeniable but research efforts in this area have been modest, to great extent due to the absence of established, specific experimental models, especially in preclinical research.

The intracutaneous injection of histamine or proteases elicits itch, and may be used as an experimental model for itch studies (Cormia, F. E., J. Invest. Derm. 19, 21 (1952); Shelley, W. B. and Arthur, R. P., Arch. Derm. (Chicago) 26, 296, 323 (1957)]. It was, therefore, postulated that these agents are involved as mediators in various itching conditions. Since histamine was believed to be the primary mediator of the itch sensation, conventional itch therapy involves $H_1$-antihistamines as a first-line medication. However, antihistamines have no general anti-pruritic effect, in many instances they are either ineffective or only partially effective. The physician is often obliged to resort to glucocorticoids to relieve pruritus but the potential undesirable side effects from glucocorticoid therapy are of great concern. Glucocorticoids cause skin atrophy and are absorbed systemically to cause Cushings disease-like effects. It has been concluded that although histamine is undoubtedly a potent pruritogen, at least one other itch-producing substance is involved in the clinically encountered spectrum of diseases where itch is a major symptom.

Although it is known that experimental pruritus may be evoked in human skin by the local administration of diverse pharmacologically active substances, the majority of which cause inflammation, demonstration that a chemical substance causes an itch sensation when locally administered does not necessarily mean that it is involved (as a mediator) in diseases in which itching is a symptom. Substances which have been reported to evoke or facilitate the itch sensation in human skin have not led to accepted anti-itch medications in those instances where compositions of matter are available to block the synthesis or activity of such substances. For example, according to Hagermark et al., *J. Invest. Dermatol.* 69, 527–539 (1977), prostaglandins $E_2$ and $H_2$ produce itch in human skin and potentiate the itch evoked by histamine. However, according to an earlier article by Hagermark [*Acta Dermatovener* 53, 363–368 (1973)) a known inhibitor of $PGE_2$ synthesis, aspirin, did not act as an anti-pruritic agent, rather it actually prolonged experimental itch produced by trypsin or histamine. These experimental findings are amply supported by clinical experience where drugs like aspirin and indomethacin are not generally regarded as useful in treating itch.

The pruritogenic activity of other substances has been attributed to an indirect mechanism involving histamine release, these postulates being based on the activity systemically administered or locally injected $H_1$-antihistamines. Thus, synthetic platelet activating factor (PAF) has been reported to cause pruritus in human skin [Fjellner and Hagermark, *Acta Derm. Venereol.* 65, 409–412 1985)] "via indirect and mainly histamine-dependent mechanism". Based upon their experimental findings, the authors concluded that PAF probably produced itch in human skin by release of mast cell bound histamine.

Given the complicating factors which may confound interpretation of itching studies, proof of involvement of a substance in mediating itch is provided only by studies which demonstrate that a composition of matter which interferes with the synthesis of pharmacological action of the substance in question attenuates pruritus in either an experimental model of itching disease or in a study involving clinically encountered itch. Further, the beneficial effect of such a composition of matter in relieving itch should be demonstrated as independent of the actions of histamine.

SUMMARY OF THE INVENTION

The present invention is based on the unexpected finding that platelet activating factor (PAF) is a very potent pruritogen and platelet activating factor antagonists (PAF antagonists) of highly diverse structures prevent itching episodes of allergic origin and the further unexpected finding that PAF antagonists are more potent in relieving itch than in relieving inflammation. The previously unrecognized antipruritic activity of such PAF antagonists is demonstrated as being independent of histaminergic mechanisms.

In one aspect, the present invention relates to a method for treating pruritus by administering a therapeutically effective amount of a PAF antagonist to a mammal afflicted with pruritus. The PAF antagonists may, for example, be selected from synthetic PAF analogues, natural products isolated from plants having PAF antagonist activity, and triazolobenzodiazepines. The PAF antagonists are preferably applied topically to the afflicted site but systemic such as oral, parenteral, nasal and intrarectal administration, is also possible.

In another aspect, the invention relates to the use of PAF antagonists in the preparation of pharmaceutical compositions intended for the treatment of pruritus.

In yet another aspect, the invention relates to the use of PAF antagonists in treatment of idiopathic itching, that is, itch which occurs spontaneously, without an underlying or identifiable physiological cause.

DETAILED DESCRIPTION OF THE INVENTION

Platelet activating factor (PAF) is a term coined by Benveniste et al. [J. Exp. Med. 136, 1356–137 (1972)] to describe a fluid phase mediator of unknown chemical structure. This mediator has later been identified as a phospholipid autocoid, which structurally is 1-0-alkyl-2-acetyl-sn-glycero-3-phosphocholine of the formula (I)

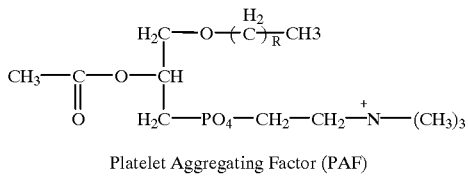

Platelet Aggregating Factor (PAF)

wherein R is 15 or 17, i.e. the alkyl moiety is hexadecyl or octadecyl. The isolation, chemical synthesis and biological and biochemical characteristics of PAF are, for example, disclosed by Hanahan and Kumar in *Prog. Lipid Res.* 26, 1–28(1987).

PAF is not stored in cells but is synthesized in response to appropriate stimuli by a two-step process. The precursor 1-o-alkyl-(R)acyl-glycero-3-phosphatidylcholine is converted to lyso-PAF by phospholipase $A_2$ and subsequent acetylation results in PAF formation. In fact lyso-PAF is both a precursor and a metabolite of PAF. PAF is known to be an important factor of physiological reactions including platelet aggregation, inflammation, contraction of smooth muscle, alterations in the respiratory and circulatory systems, etc. PAF antagonists have been discovered comparatively recently, and comprise a series of compounds of diverse structures effective in the treatment of conditions traditionally associated with PAF. The PAF antagonists reported so far in the art may be broadly classified according to their origin and structures as follows: (a) synthetic analogues of the PAF structure; (b) natural products isolated from plants; (c) triazolobenzo-diazepines. By virtue of these antagonists, it has become apparent that PAF exerts its known biological effects by stimulating specific PAF-sensitive receptors.

A PAF antagonist, which is a synthetic analogue of the PAF structure is the compound of formula (II),

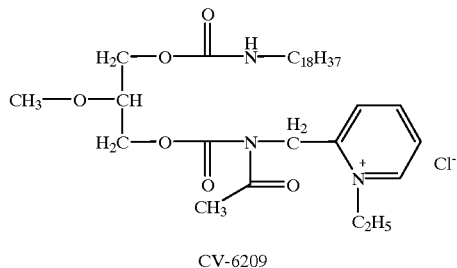

CV-6209 which was disclosed by Terashita et al, in *J. Pharm. Exp. Ther.* 242, 263–268 (1987). Other synthetic lipid PAF inhibitors are described In the Published European Patent Application 0,157,609 A2 as preventive or therapeutic agents for a variety of circulatory diseases and allergic disorders and as anti-neoplastic agents.

According to the U.S. Pat. No. 4,734,280, PAF induced maladies can be effectively treated by the administration of a ginkgolide or a ginkgolide derivative. Ginkgolides were originally isolated from Ginkgo Biloba extracts, and their commonly available representatives include Ginkgolide A, Ginkgolide B, Ginkgolide C, and Ginkgolide M, of which Ginkgolide B (BN 52021) of the formula (III)

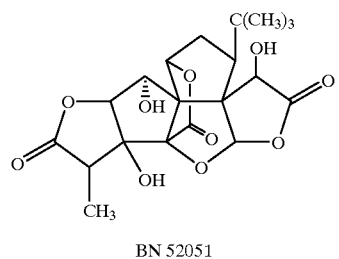

BN 52051 was found to be the most effective [Braquet et al, *Les Actualites de Chimie Therapeutique* (Paris) 13, 237–254 (1986)]. Known derivatives of ginkgolides include the mono-acetate, the tri-acetate, and the tetrahydro and acetyl derivatives. According to the test data disclosed in the U.S. Pat. No. 4,734,280, these compounds show platelet aggregation inhibiting and antianaphylactic activities, and exhibit a protective effect against transvascular fluid escape and shock.

PAF antagonist triazolobenzodiazepine derivatives were, for example, described by Kornecki et al, Science 226, 1454–1456 (1986), and are disclosed in the U.S. Pat. No. 4,820,703, and in the Published European Patent Application No. 0,194,416 A1. Typical representatives of this class of PAF antagonists are the compounds of formulas (IV) and (V):

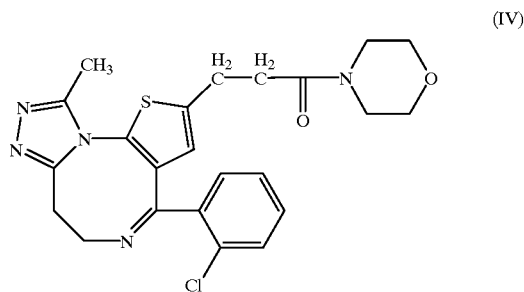

WEB 2086

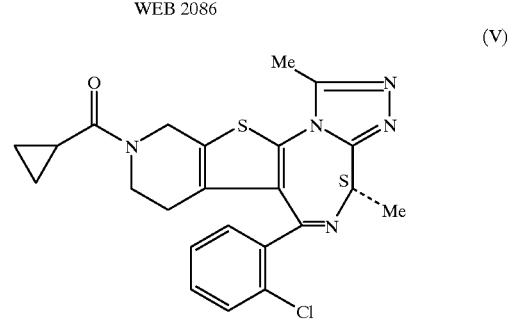

E-6123

WEB 2086 is disclosed in the above-cited Published European Patent Application. E-6123 has been described in *Chem. Pharm. Bull*, 39, (12), Miyazawa Shuhei, et al. (1991). These compounds are described as useful for the prevention or treatment of various PAF-induced diseases, such as diseases associated with platelet aggregation, certain immediate allergic reactions caused by PAF, pain, edema, alteration in the respiratory and circulatory system, etc.

In studies intended to identify pruritogenic substances 30 other than histamine, the inventor of the present application has discovered that PAF is a most potent itch producing substance, capable of producing marked itching at a dose of 1 μg applied topically to the eye. Woodward et al., *J. Pharmacol. Exp. Ther*. 272, 758 (1995)

In a prior study, however, the inventors found that PAF does not result in increased microvascular permeability and eosinophil infiltration, both of which are well-established inflammatory events in allergy Woodward et al., *Eur. J. Pharmacol*. 168, 23, (1989).

Moreover, certain known PAF antagonists were found to specifically block the pruritogen activity of PAF and, more importantly, were found to significantly reduce the pruritus associated with an experimental model of itching diseases. Although PAF had been described as a substance that causes pruritus in human skin by Fjellner and Hagermark, supra, its action was associated with histamine liberation. Accordingly, it was entirely unexpected that PAF antagonists are capable of relieving itch, and do so in a non-histamine related fashion, or that PAF antagonists are more effective at relieving itching than inflammation.

The term "PAF" antagonist as used in accordance with the present invention, refers to synthetic or naturally occurring compounds known in the art or hereinafter discovered, that are effective in the treatment of pruritus via interfering with the pruritogenic action of PAF. This definition includes, but is not restricted to the above-mentioned three classes of PAF antagonists, the preferred representatives being compounds of formulae (II), (III). (IV) and (V) as hereinabove defined.

The term "treatment" is used to cover all aspects of the control of itching including prophylaxis and therapy.

The term "therapeutically effective amount" and grammatical variations thereof, as used herein refer to sufficient quantities of the active compound that can produce the desired therapeutic effect when administered to a mammal afflicted with pruritus. The term "therapeutic effect" is used herein in a broad sense and includes prophylactic effects.

In accordance with the present invention, the PAF antagonists are preferably applied to the afflicted area topically, in admixture with pharmaceutical carriers, in the form of topical pharmaceutical compositions. Such compositions include solutions, suspensions, lotions, gels, creams, ointments, emulsions, skin patches, etc. All of these dosage forms, along with methods for their preparation, are well known in the pharmaceutical and cosmetic art. Typically, such topical formulations contain the active ingredient in a concentration range of 0.001 to 10 mg/ml, in admixture with suitable vehicles. Other desirable ingredients for use in such anti-pruritic preparations include preservatives, co-solvents, viscosity building agents, carriers, etc.

For ophthalmic application, preferably solutions are prepared typically containing from about 0.001 to about 10 mg/ml, preferably from about 0.1 to about 6 mg/ml of active ingredient, and a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and/or penetration enhancers.

The preferred vehicle that may be used in the ophthalmic solutions of the present invention is purified water, more preferably a physiological saline solution. Additional suitable vehicles include but are not restricted to, viscosity agents such as polyvinyl alcohol, povidone, hydroxypropyl methyl cellulose, poloxamers, carboxymethyl cellulose, carbomer and hydroxyethyl cellulose.

Preferred preservatives that may be used in the ophthalmic formulations of the present invention include, but are not limited to, benzalkonium. chloride, chlorobutanol, thimerosal, phenylmercuric acetate and phenylmercuric nitrate.

Penetration enhancers may, for example, be surface active agents; certain organic solvents, such as di-methylsulfoxide and other sulfoxides, dimethyl-acetamide and pyrrolidone; certain amides of heterocyclic amines, glycols (e.g. propylene glycol);propylene carbonate; oleic acid; alkyl amines and derivatives; various cationic, anionic, nonionic, and amphoteric surface active agents; and the like.

Tonicity adjustors may be added as needed or convenient. They include, but are not limited to, salts, particularly sodium chloride, potassium chloride, mannitol and glycerin, or any other suitable opthalmically acceptable tonicity adjustor.

Various buffers and means for adjusting pH may be used so long as the resulting preparation is ophthalmically acceptable.

Accordingly, buffers include acetate buffers, citrate buffers, phosphate buffers and borate buffers for ophthalmic use.

In a similar vein, an ophthalmically acceptable antioxidants for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place or in conjunction with it.

In addition to topical therapy, other routes of administration such as oral, parenteral, nasal inhalation, and intrarectal are also contemplated. For these uses, additional conventional pharmaceutical preparations such as tablets, granules, powders, capsules, and sprays may be preferentially required. In such formulations further conventional additives such as binding-agents, wetting agents, propellants, lubricants, and stabilizers may also be required.

The route of administration, dosage form, and the effective amount vary according to the potency of the selected PAF antagonist, its physicochemical characteristics, and according to the condition to be treated. The selection of proper dosage is well within the skill of an ordinary skilled physician. Topical formulations are usually administered up to four-times a day. A typical dosage of ophthalmic solutions is 1–2 drops in the afflicted eye up to four-times a day.

The use of PAF antagonists as anti-pruritics is advantageous in that they relieve itching by a mechanism independent of histaminergic compounds. Thus, they may be effective in itching diseases which are refractory to antihistamine therapy and may be combined with H1-antihistamines to provide superior therapy via additive or synergistic interaction.

A more complete appreciation of the invention may be obtained from the following Examples. As a means of providing an atraumatic experimental model of itching, the conjunctiva was used as a convenient tissue site. Pruritogenic agents may be administered to the conjunctiva without the need to traumatize the tissue by injection or scarification. The itch sensation is elicited peripherally by local, atraumatic application of the pruritogen. Of equal importance is the ability of this model to identify locally acting anti-pruritic agents without concerns regarding local tissue trauma or, in the case of systemically administered agents, sedation.

EXAMPLE 1

The pruritogenic activity of numerous and structurally diverse autocoids was examined as follows. A 20 μl drop of a solution of the particular autocoid under evaluation was topically administered to one albino guinea-pig eye, the contralateral eye received 20 Al of vehicle as a control. For PAF studies, the R=15 version of formula I was used and was taken up in 0.5% ultra pure bovine serum albumin. The guinea pig was then replaced in its cage and the number of scratching episodes was recorded over the 15 subsequent minute period. The retention of the experimental animal in familiar surroundings is an important factor in experimental design. Scratching, which is the typical mammalian behavioral response to the itch sensation, provides an indication of the intensity of the perceived itch sensation and can be quantified by recording the frequency at which itch-scratch episodes occur per unit time: 15 minutes in the case of these examples. The data obtained on several autocoids at physiological dose levels is summarized in Table 1.

TABLE 1

COMPARISON OF THE PRURITOGENIC ACTIVITY OF AUTOCOIDS

| AUTOCOID | DOSE ($\mu$g) | NO. OF SCRATCH EPISODES (X + SEM) |
|---|---|---|
| PAF | 1 | 6.42 ± 1.26 |
| PAF | 10 | 10.17 ± 1.31 |
| PAF | 100 | 13.46 ± 0.88 |
| HISTAMINE | 1 | 1.67 ± 0.45 |
| HISTAMINE | 10 | 8.42 ± 1.12 |
| HISTAMINE | 100 | 20.33 ± 2.55 |
| HISTAMINE | 1000 | 20.33 ± 2.18 |
| PROSTAGLANDIN $D_2$ | 1 | 0.75 + 0.25 |
| PROSTAGLANDIN $D_2$ | 10 | 4.42 + 1.36 |
| PROSTAGLANDIN $D_2$ | 100 | 3.08 + 0.47 |
| PROSTAGLANDIN $E_2$ | 1 | 2.25 + 0.66 |
| PROSTAGLANDIN $E_2$ | 10 | 3.08 + 0.48 |
| PROSTAGLANDIN $E_2$ | 100 | 8.17 + 1.54 |
| PROSTAGLANDIN $F_{2\alpha}$ | 100 | 1.75 + 0.37 |
| CARBACHOL | 10 | 0.75 + 0.33 |
| CARBACHOL | 100 | 0.83 + 0.24 |
| CARBACHOL | 1000 | 3.08 + 0.67 |
| METHACHOLINE | 10 | 0.50 ± 0.19 |
| METHACHOLINE | 100 | 0.67 + 0.43 |
| METHACHOLINE | 1000 | 2.17 + 0.77 |
| ECF-A (L-alanylglycyl-L-seryl-L-glutamic acid) | 1000 | 1.42 + 0.47 |
| ECF-A (L-valylglycyl-L-aspartyl-L-glutamic acid | 100 | 0.92 ± 0.26 |
| LEUKOTRIENE $B_4$ | 10 | 0.42 ± 0.23 |
| LEUKOTRIENE $C_4$ | 10 | 0.58 ± 0.36 |
| LEUKOTRIENE $D_4$ | 1 | 0.83 ± 0.41 |
| LEUKOTRIENE $D_4$ | 10 | 0.50 ± 0.34 |
| LEUKOTRIENE $E_4$ | 1 | 0.58 ± 0.42 |
| LEUKOTRIENE $E_4$ | 10 | 0.25 ± 0.13 |
| 5-Hydroxytetraemoic Acid | 10 | 0.33 ± 0.22 |
| 12-Hydroxytetraemoic Acid | 10 | 0.08 ± 0.08 |
| 15-Hydroxytetraemoic Acid | 10 | 0.08 ± 0.08 |
| Bradykinin | 10 | 6.50 ± 0.23 |
| Bradykinin | 100 | 4.00 ± 0.90 |
| LYSO-PAF | 1 | 0.92 ± 0.26 |
| LYSO-PAF | 10 | 2.67 ± 0.73 |
| LYSO-PAF | 100 | 13.0 ± 1.58 |
| NORMAL SALINE | — | 1.17 ± 0.42 |
| 3.6% SALINE | — | 2.25 ± 0.57 |
| 10 MM ACETIC ACID | — | 0.42 ± 0.19 | n = 12, Values are Mean + SEM

It is apparent from Table 1 that PAF is the most potent pruritogenic agent. The relatively weak activity of lyso-PAF is consistent with a receptor mediated effect. The virtual absence of an itch-scratch response to pain producing stimuli such as hypertonic saline and 10 mM acetic acid provides further validation of the model.

EXAMPLE 2

The ability of a 30 minute topical pretreatment with selected PAF antagonists to attenuate PAF induced pruritus is shown in Table 2.

TABLE 2

| TREATMENT REGIMEN Compound of formula: | CONTROL GROUP | TREATED GROUP |
|---|---|---|
| (II) (10 mg/ml) vs 1 $\mu$g PAF | 6.42 ± 1.13 | 2.67 ± 0.68* |
| (II) (10 mg/ml) vs 10 $\mu$g PAF | 10.08 ± 0.82 | 6.50 ± 1.09* |
| (III) (10 mg/ml) vs 10 $\mu$g PAF | 14.33 ± 1.46 | 8.42 ± 1.37* |
| (IV) (5 mg/ml) vs 1 $\mu$g PAF | 4.00 + 0.67 | 0.33 ± 0.19** |
| (IV) (5 mg/ml) vs 10 $\mu$g PAF | 11.33 ± 1.53 | 5.25 ± 0.98** |
| Pyrilamine (0.1 mg/ml) vs 1 $\mu$g PAF | 4.67 ± 0.82 | 4.17 ± 0.91 |
| Pyrilamine (0.1 mg/ml) vs 10 $\mu$g PAF | 13.67 ± 1.70 | 14.25 ± 1.75 |

Values are mean + SEM
*$p < 0.05$;
**$p < 0$-$01$;
n = 12

Table 2 demonstrates that PAF induced pruritus may be blocked by PAF antagonists but not by the antihistamine pyrilamine: this indicates that PAF does not evoke a pruritic effect by an indirect mechanism involving histamine.

EXAMPLE 3

In addition to pharmacological studies on pruritogenic autocoids, the conjunctiva may be used as a convenient site for modeling diseases where itching is a major symptom. In animals presensitized to a particular antigen, subsequent topical challenge with that antigen results in conjunctival itching. This may be regarded as an experimental model of itching which has general relevance to clinically encountered pruritus. In the studies described herein, chicken ovalbumin was used as an antigenic substance and the ability of PAF antagonist pretreatment to block the itching response was examined (Table 3).

TABLE 3

| EFFECT OF PAF ANTAGONISTS ON ALLERGIC ITCHING | | |
|---|---|---|
| TREATMENT REGIMEN Compound of formula: | CONTROL GROUP | TREATED GROUP |
| (II) (1 mg/ml) vs 100 $\mu$G antigen | 14.38 ± 2.21 | 7.62 ± 0.96* |
| (III) (10 mg/ml) vs 100 $\mu$G antigen | 12.25 ± 1.72 | 6.87 ± 1.61* |
| (IV) (10 mg/ml) vs 10 $\mu$G antigen | 11.00 ± 2.50 | 5.00 ± 1.10* |

*$p < 0.05$ n = 8 – 10

EXAMPLE 4

A study was performed to compare the efficacy of several PAF antagonists in treating pruritus to their efficacy in treating inflammation. Two of the triazolobenzo-diazepine compounds described supra as formulas (IV) and (V) (WEB 2086 and E-6123) respectively) were evaluated for their ability to reduce or eliminate scratching episodes as an indicator of suppression of pruritus induced by the introduction of ovalbumin into the conjunctiva of ovalbumin sensitized mice. These results were compared to measurements of relief of inflammation as indicated by a decrease in plasma extravasation in the bulbar conjunctival area of the eye (Table 4).

TABLE 4

| Vehicle | 0.5% WEB 2086 | Vehicle | E-6123 |
|---|---|---|---|
| ALLERGIC ITCHING | | | |
| Mean = 11.0 | Mean = 5.0 | Mean = 7.50 | Mean = 2.42 |
| SEM = ± 2.5 | SEM = ± 1.1 | SEM = ± 0.59 | SEM = ± 0.30 |
| ALLERGIC INFLAMMATION | | | |
| Mean = 3.64 | Mean = 4.0 | Mean = 3.38 | Mean = 2.50 |
| SEM = ± 1.01 | SEM = ± 0.74 | SEM = ± 0.69 | SEM = ± 0.41 |

These results demonstrate that PAF is a major mediator of itching diseases and that administration of a PAF antagonist provides an effective method for treating pruritus. It is also demonstrated that In addition, PAF antagonists may also be used in combination with antihistamines or glucocorticoids.

It is understood that this invention may be embodied in a variety of forms without departing from the spirit or essential characteristics. Thus,however detailed the foregoing may appear in text, it should not be construed as limiting the overall scope hereof; rather, the ambit of the present invention is to be governed only by the lawful construction of the appended claims.

We claim:

1. A method of treating pruritus consisting essentially of administering a therapeutic amount of a PAF antagonist in the absence of an antihistamine to a mammal having pruritus but without experiencing PAF induced inflammation.

2. The method of claim 1, wherein said PAF antagonist derivative is a compound of formula (II)

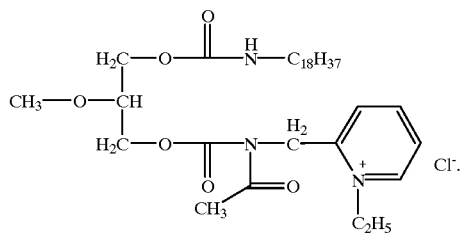

3. The method of claim 1, wherein said PAF antagonist is a ginkgolide or a ginkgolide derivative.

4. The method of claim 3, wherein said ginkgolide or a ginkgolide derivative is selected from the group of Ginkgolide A, Ginkgolide B, Ginkgolide C and Ginkgolide M, and derivatives thereof.

5. The method of claim 4, wherein said ginkgolide is Ginkgolide B of the formula (III)

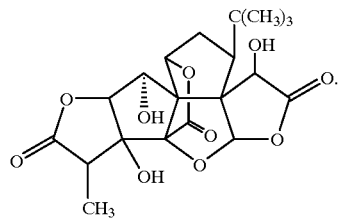

6. The method of claim 1, wherein said PAF antagonist is a triazolobenzodiazepine.

7. The method of claim 6, wherein said triazolobenzodiazepine is a compound of formula (IV)

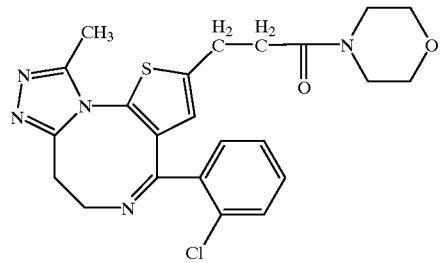

or formula (V)

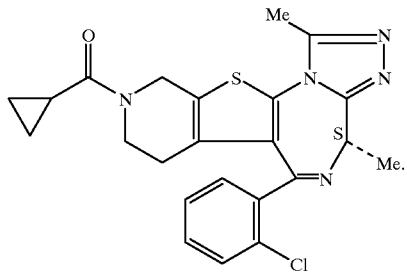

8. The method of claim 1, wherein said PAF antagonist is applied topically to the site afflicted with pruritus.

9. The method of claim 1, wherein said PAF antagonist is administered systemically.

10. The method of claim 1, wherein said PAF antagonist is administered in the form of a pharmaceutical composition comprising a therapeutically effective amount of said PAF antagonist as active ingredient, in admixture with a pharmaceutical carrier.

11. The method of claim 10, wherein said pharmaceutical composition is formulated in a form suitable for topical application.

12. The method of claim 11, wherein said pharmaceutical composition is formulated as an ophthalmic solution.

13. A method of treating pruritus consisting essentially of administering an amount of a PAF-antagonist in the absence of an antihistamine that is therapeutically effective for alleviating itch without being sufficient to treat PAF-induced inflammation.

14. A method of treating idiopathic pruritus consisting essentially of administering to a mammal in need thereof a therapeutic amount of a PAF antagonist in the absence of an antihistamine and wherein the mammal is not suffering from a concurrent lesion known to induce itching.

15. The method of claim 14, wherein said PAF antagonist derivative is a compound of formula (II)

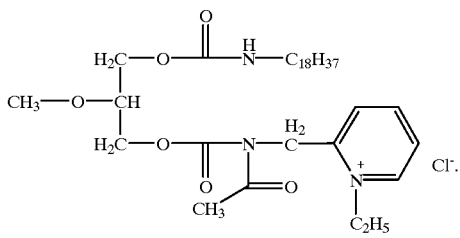

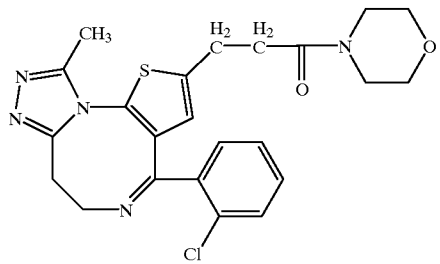

16. The method of claim 14, wherein said PAF antagonist is a ginkgolide or a ginkgolide derivative.

17. The method of claim 16, wherein said ginkgolide or a ginkgolide derivative is selected from the group of Ginkgolide A, Ginkgolide B, Ginkgolide C and Ginkgolide M, and derivatives thereof.

18. The method of claim 17, wherein said ginkgolide is Ginkgolide B of the formula (III)

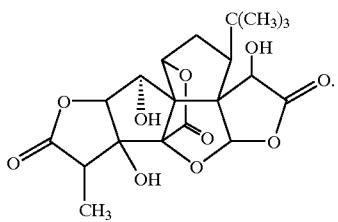

19. The method of claim 14, wherein said PAF antagonist is a triazolobenzodiazepine.

20. The method of claim 19 wherein said triazolobenzodiazepine is a compound of formula (IV)

or formula (V)

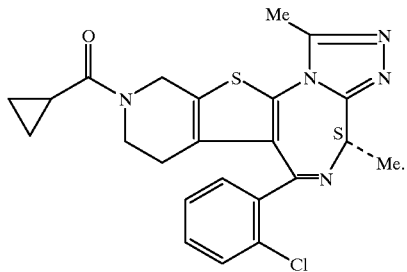

21. The method of claim 14, wherein said PAF antagonist is applied topically to the site afflicted with pruritus.

22. The method of claim 14, wherein said PAF antagonist is administered systemically.

23. The method of claim 14, wherein said PAF antagonist is administered in the form of a pharmaceutical composition consisting essentially of a therapeutically effective amount of said PAF antagonist as active ingredient, in admixture with a pharmaceutical carrier in the absence of an antihistamine.

24. The method of claim 23, wherein said pharmaceutical composition is formulated in a form suitable for topical application.

25. The method of claim 24, wherein said pharmaceutical composition is formulated as an ophthalmic solution.

* * * * *